United States Patent [19]

Sheldrake

[11] Patent Number: 5,258,547
[45] Date of Patent: Nov. 2, 1993

[54] PROCESS FOR PREPARING HALOGENATED COMPOUNDS

[75] Inventor: Gary N. Sheldrake, Huddersfield, England

[73] Assignee: Imperial Chemical Industries plc, London, Great Britain

[21] Appl. No.: 818,329

[22] Filed: Jan. 9, 1992

[30] Foreign Application Priority Data

Jan. 11, 1991 [GB] United Kingdom ............... 9100654

[51] Int. Cl.$^5$ ................... C07C 273/00; C07C 63/36; C07C 49/00
[52] U.S. Cl. .................... 560/226; 560/100; 560/184; 560/8; 560/227; 560/229; 562/490; 562/586; 562/602; 562/605; 562/840; 562/849; 562/856; 562/864; 568/303; 568/323; 568/348; 568/364; 568/365
[58] Field of Search ............ 560/8, 100, 184, 226, 560/227, 229; 562/490, 586, 602, 605, 840, 849, 856, 864; 568/303, 323, 348, 364, 365

[56] References Cited

U.S. PATENT DOCUMENTS

4,252,820  2/1981  Lantzch et al. .............. 424/304

FOREIGN PATENT DOCUMENTS

| 008340 | 2/1979 | European Pat. Off. |
| 003336 | 8/1979 | European Pat. Off. |
| 0053812 | 4/1977 | Japan ................ 562/605 |
| 0158134 | 8/1985 | Japan ................ 562/605 |
| 1520443 | 8/1978 | United Kingdom . |

*Primary Examiner*—José G. Dees
*Assistant Examiner*—Keith MacMillan
*Attorney, Agent, or Firm*—William E. Dickheiser

[57] ABSTRACT

A process for preparing halogenated compounds of formula $RCY(Z)CH_2CH(X)C(CH_3)CH_2COR^1$ where X, Y and Z are halo, R is alkyl, halo, haloalkyl or aryl, and $R^1$ is hydroxy, halo, alkoxy, alkyl or haloalkyl, or the residue of a pyrethroidal alcohol, in which a compound of formula $CH_2=CHC(CH_3)_2COR^1$ is reacted with a sulphonyl halide of formula $RCY(Z)SO_2X$. The process avoids the use of volatile halocarbons in the production of valuable intermediates for insecticides.

8 Claims, No Drawings

PROCESS FOR PREPARING HALOGENATED COMPOUNDS

This invention relates to a process for preparing valuable intermediates for pesticides. More particularly it relates to a process for preparing halogenated compounds useful as intermediates for insecticides.

It is known from UK Patent No. 1520443 that halogenated esters such as alkyl 3,3-dimethyl-4,6,6,6-tetrahalohexanoates can be converted to alkyl 3-(2,2-dihalovinyl)-2,2-dimethylcyclopropane carboxylates by treatment with base, and that the corresponding cyclopropane carboxylic acids can be converted to esters with, for example, 3-phenoxybenzyl alcohol to provide valuable insecticidal products.

Hitherto the preparation of these halogenated esters has involved the reaction of volatile haloalkanes, such as carbon tetrachloride and 1,1,1-trichlorotrifluoroethane with an unsaturated ester, and the process has had to conducted in chemical plant and under conditions in which the components could be contained so as to prevent discharge of the volatiles to the atmosphere.

The present invention concerns a new process in which the volatile haloalkanes are replaced by relatively non-volatile reactants, thereby substantially reducing the possibility of escape of volatile haloalkane components to the atmosphere.

Accordingly the present invention provides a process for the preparation of a compound of formula I: wherein X, Y and Z are each selected from halo, preferably chloro, fluoro or bromo; R is halo, alkyl or haloalkyl or aryl which may optionally be substituted with halo; and $R^1$ is selected from hydroxy, halo, preferably chloro or bromo, alkoxy of up to 6 carbon atoms, alkyl of up to 4 carbon atoms which may optionally be substituted with halo; or $R^1$ represents a group —$OR^2$ derived from an alcohol $R^2OH$ esters of which with 3-(2,2-dichlorovinyl)-2,2-dimethylcyclopropane carboxylic acid are insecticidal, including those where $R^2$ represents alkaryl, preferably benzyl which may optionally be substituted in the methylene moiety with cyano, or alkynyl of up to 4 carbon atoms, and in the phenyl moiety by up to 5 substituents selected from halo, preferably chloro or fluoro, alkyl of up to 4 carbon atoms, preferably methyl, haloalkyl of up to 4 carbon atoms, preferably trifluoromethyl, alkoxyalkyl of up to 4 carbon atoms, preferably methoxymethyl, haloalkoxy, preferably trifluoromethoxy, phenoxy and halophenoxy; wherein a compound of formula II: is reacted with a sulphonyl halide of formula III:

Particularly useful compounds which can be prepared by the process of the invention include:
methyl 3,3-dimethyl-4,6,6,6-tetrachlorohexanoate,
methyl 3,3-dimethyl-4,6,6,6-tetrabromohexanoate,
ethyl 3,3-dimethyl-4,6,6,6-tetrachlorohexanoate,
methyl 3,3-dimethyl-4-bromo-6,6,6-trifluorohexanoate,
4,4-dimethyl-1,5,7,7,7-pentachloroheptan-2-one,
4,4-dimethyl-1,5,7,7-tetrachloro-7-(4-chlorophenyl)-heptan-2-one,
3,3-dimethyl-4,6,6,6-tetrachlorohexanoic acid,
methyl 3,3-dimethyl-4,6,6-trichloro-7,7,7-trifluoroheptanoate,
ethyl 3,3-dimethyl-4,6,6-trichloro-7,7,7-trifluoroheptanoate,
methyl 3,3-dimethyl-4,6,6-trichloro-6-(4-chlorophenyl)-hexanoate,
benzyl 3,3-dimethyl-4,6,6-trichloro-7,7,7-trifluoroheptanoate,
2,6-dichlorobenzyl 3,3-dimethyl-4,6,6-trichloro-7,7,7-trifluoroheptanoate,
4-methyl-2,3,5,6-tetrafluorobenzyl 3,3-dimethyl-4,6,6-trichloro-7,7,7-trifluoroheptanoate,
pentafluorobenzyl 3,3-dimethyl-4,6,6,6-tetrachlorohexanoate,
2,3,5,6-tetrafluorobenzyl 3,3-dimethyl-4,6,6,6-tetrachlorohexanoate,
2-methyl-3-phenylbenzyl 3,3-dimethyl-4,6,6-trichloro-7,7,7-trifluoroheptanoate,
3-phenoxybenzyl 3,3-dimethyl-4,6,6,6-tetrachlorohexanoate,
α-cyano-3-phenoxybenzyl 3,3-dimethyl-4,6,6,6-tetrachlorohexanoate,
α-cyano-3-phenoxybenzyl 3,3-dimethyl-4,6,6,6-tetrabromohexanoate,
α-cyano-4-fluoro-3-phenoxybenzyl 3,3-dimethyl-4,6,6,6-tetrachlorohexanoate,
α-cyano-3-phenoxybenzyl 3,3-dimethyl-4,6,6-trichloro-7,7,7-trifluoroheptanoate, and
α-cyano-4-fluoro-3-phenoxybenzyl 3,3-dimethyl-4,6,6-trichloro-7,7,7-trifluoroheptanoate.

Compounds of formula II which are useful in the process of the invention include the following:
methyl 3,3-dimethylpent-4-enoate,
ethyl 3,3-dimethylpent-4-enoate,
4,4-dimethyl-1-chlorohex-5-en-2-one,
3,3-dimethylpent-4-enoic acid,
benzyl 3,3-dimethylpent-4-enoate,
2,6-dichlorobenzyl 3,3-dimethylpent-4-enoate,
4-methyl-2,3,5,6-tetrafluorobenzyl 3,3-dimethylpent-4-enoate,
pentafluorobenzyl 3,3-dimethylpent-4-enoate,
2,3,5,6-tetrafluorobenzyl 3,3-dimethylpent-4-enoate,
2-methyl-3-phenylbenzyl 3,3-dimethylpent-4-enoate,
3-phenoxybenzyl 3,3-dimethylpent-4-enoate,
α-cyano-3-phenoxybenzyl 3,3-dimethylpent-4-enoate, and
α-cyano-4-fluoro-3-phenoxybenzyl 3,3-dimethylpent-4-enoate.

Compounds of formula III which are useful in the process of the invention include:
trichloromethane sulphonyl chloride,
tribromomethane sulphonyl bromide,
trifluoromethane sulphonyl bromide,
1,1-dichloro-2,2,2-trifluoromethane sulphonyl chloride, and
1,1-dichloro-1-(4-chlorophenyl)methane sulphonyl chloride.

The process may be conducted in the presence or absence of a solvent or liquid diluent for the reactants. Where a solvent or diluent is used it is convenient to employ any liquid material which is chemically inert under the conditions of the process, which permit the process to proceed at the temperature desired and is readily separated from the resultant product, by for example evaporation or fractional distillation. Suitable solvents include aromatic hydrocarbon solvents such as toluene, or xylene, or aliphatic solvents such as esters, ketones and alkanes, or halogenated solvents such as haloalkanes.

The process may be conducted at any temperature at which reaction occurs at a reasonable rate. The rate of reaction increases with temperatures and it is frequently convenient to conduct the reaction at elevated temperatures, for example, within the range 50°–150° C., the upper limit being defined by the reflux temperature of the solvent or diluent where this is employed. The duration of the reaction will be dependent upon the rate of reaction at the temperature used but will generally be within the range from 1 to 60 hours, and preferably 3 to 40 hours.

The rate of reaction can often be increased, or the reaction temperature reduced, by the use of catalysts which promote the reaction. Free radical catalysts appear to be useful for this purpose, including for example organic peroxides such as benzoyl peroxide, azo compounds such as azobisisobutyronitrile, and the like. Another class of catalysts which are useful are useful are complexes of certain metals with phosphines, such as tris-(triphenylphosphinyl)ruthenium(II) dichloride.

The sulphonyl halides of formula III are conveniently prepared by oxidation of the corresponding sulphenyl halides of formula IV:

The oxidation of sulphenyl halides of formula IV to the sulphonyl halides of formula III appears not to have been described previously. This oxidation can conveniently be carried out by the use of hydrogen peroxide, or paracids, such as peracetic or perbenzoic acid, for example by treating the sulphenyl halide with a mixture of hydrogen peroxide and glacial acetic acid. The process can be conducted at elevated temperatures if desired.

In a further aspect therefore the invention provides a process for obtaining a compound of formula I as described above in which, in a preliminary step the sulphonyl halide of formula III is obtained by oxidation of the corresponding sulphenyl halide of formula IV.

The sulphenyl halides of formula IV may be obtained by the hydrogenolysis of suitable precursors, such as a disulphide of formula V: or a thioether of formula VI: wherein halogenation of the methylene group bearing the R group is accompanied by halogenolysis of the sulphur-benzyl bond giving rise to the sulphenyl halide of formula III and benzyl halide.

Further details of the process of the invention are given in the Examples which follow.

EXAMPLE 1

This Example illustrates the preparation of bis-(2,2,2-trifluoromethyl) disulphide.

A mixture of 2,2,2-trifluoroethyl bromide (9.8 g), sodium sulphide nonahydrate (14.4 g), sulphur (1.9 g), hexadecyl tributyl phosphonium bromide (1.0 g) and water (18.0 g) was charged to a Carius tube under a nitrogen atmosphere and the tube sealed. The tube was heated to 70° C. for 8 hours, cooled and the contents subjected to steam distillation to give bis-(2,2,2-trifluoroethyl) disulphide as an oil in a yield of 67° C. The product was identified by GC-mass spectroscopy.

EXAMPLE 2

This Example illustrates the preparation of 1,1-dichloro-2,2,2-trifluoroethane sulphenyl chloride.

Sulphenyl chloride (4.46 g) was added dropwise to a solution of bis-(2,2,2-trifluoroethyl) disulphide (1.0 g) in dichloromethane (5.0 cm$^3$) at the ambient temperature under a dry nitrogen atmosphere. After 3 hours the yield of the desired product was estimated at 60% by gas-liquid chromatography. The product was identical to that obtained in Example 4 below.

EXAMPLE 3

This Example illustrates the preparation of 2,2,2-trifluoroethylthiomethylbenzene.

A mixture of 1-chloro-2,2,2-trifluoroethane (20 g), benzyl mercaptan (12.4 g, 99% strength), sodium hydroxide (22.0 g of a 22% aqueous solution) and hexadecyl tributyl phosphonium bromide (0.51 g) was charged to a resealable Carius tube under a nitrogen atmosphere and heated at 70° C. for 10 hours. The tube was then cooled to 0° C., unsealed and the contents separated into two layers. The lower organic layer was collected, washed with water and purified by short path distillation to give 2,2,2-trifluoroethylthiomethylbenzene, b.p. 60°–70° C./ 10 mmHg, 17.4 g (yield 84%, strength 99%). The identity of the product was confirmed by gc-mass spectroscopy and nuclear magnetic reconance, and by comparison with data provided in C. Bunyagidj et al, J Org. Chem., 1981, 46 3335.

EXAMPLE 4

This Example illustrates the preparation of 1,1-dichloro-2,2,2-trifluoroethane sulphenyl chloride.

A solution of 2,2,2-trifluoroethylthiomethylbenzene (20.0 g, strength 99%, obtained by the method of Example 3 above) in 1,1,2,2-tetrachloroethane (26.4 cm$^3$) was cooled to 0° C. and chlorine gas passed into the solution for ca 3 hours at this temperature. The orange solution thus obtained was sparged with nitrogen and subjected to fractional distillation, to give 1,1-dichloro-2,2,2-trifluoroethane sulphenyl chloride as a deep yellow oil, b.p. 63°–65° C./ 200 mbar (17.4 g, 73% strength, 60% molar yield) contaminated with residual tetrachloroethane and <1% benzyl chloride). The product was identified by gc-mass spectroscopy, and comparison with data provided by H. Fritz et al, Chem, Ber., 1989, 122, 1757.

EXAMPLE 5

This Example illustrates the preparation of 1,1-dichloro-2,2,2-trichloroethane sulphonyl chloride.

1,1-Dichloro-2,2,2-trichloroethane sulphenyl chloride (6.3 g) obtained by the method of Example 4) was dissolved in glacial acetic acid (16.0 g) at 10° C. and the solution cooled to 5° C. Hydrogen perodide (16.8 g of a 30% solution in water) was added dropwise to the solution of the sulphenyl chloride over 30 minutes after which the solution was heated to 60° C. until the yellow colour had been completely discharged (ca 2 hours). The mixture was cooled to the ambient temperature and the excess hydrogen peroxide decomposed by treatment with an aqueous solution (10% w/w) of sodium metabisulphite. The mixture separated into two phases and the lower organic layer was collected and analysed by gc-mass spectroscopy. It contained 75% w/w of the desired 1,1-dichloro-2,2,2-trifluoroethane sulphonyl chloride, indicating a molar yield of 57%. The product identify was confirmed by comparison with material prepared by the method of H.Wei-Yuan et al, Acta Chim. Sinica, 1986, 44 45 (Chemical Abstracts 105, 171793b).

EXAMPLE 6

This Example illustrates the preparation of methyl 3,3-dimethyl-4,6,6,6-tetrachlorohexanoate.

Trichloromethane sulphonyl chloride (22.5 g) is added to a solution of methyl 3,3-dimethylpent-4-enoate (8.26 g) in toluene (8.67 g) in the presence of tris-(triphenylphosphinyl)ruthenium(II) dichloride (0.2 g) and the mixture heated under an nitrogen atmosphere at the reflux temperature (ca. 111° C.) for 40 hours. The composition of the reaction mixture was then determined by gas liquid chromatography (glc). The desired product was present in an amount indicating a yield of 76% by weight based on methyl 3,3-dimethylpent-4-enoate charged, and 90% based on methyl 3,3-dimethylpent-4-enoate consumed. The identify of this product was confirmed by glc-mass spectroscopy and 3,3-dimethyl-4,6,6,6-tetrachlorohexanoate obtained by the method described in UK Patent No. 1520443.

EXAMPLE 7

This Example illustrates the preparation of methyl 3,3-dimethyl-4,6,6,6-tetrachlorohexanoate.

Trichloromethane sulphonyl chloride (44.5 g) was added to a mixture of methyl 3,3-dimethylpene-4-enoate (16.52 g), toluene (17.34 g) and benzoyl peroxide (0.563 g) and the mixture heated at 90° C. for 3.5 hours. Determination of the composition of the reaction mixture by gas-liquid chromatography indicated that the desired product was obtained in 92% yield based on methyl 3,3-dimethylpent-4-enoate charged.

EXAMPLE 8

This Example illustrates the preparation of methyl 3,3-dimethyl-4,6,6-trichloro-7,7,7-trifluoroheptanoate.

A mixture of 1,1-dichloro-2,2,2-trichloroethane sulphonyl chloride (1.5 g) and methyl 3,3-dimethylpent-4-enoate (2.0 g) was heated at 110° C. for 40 minutes and the composition determined by glc analysis. This indicated that the yield of the desired product was 79%.

EXAMPLE 9

This Example illustrates the preparation of methyl 3,3-dimethyl-4,6,6-trifluoro-7,7,7-trifluoroheptanoate.

1,1-Dichloro-2,2,2-trifluoroethane sulphonyl chloride (0.2 g) was added to a mixture of methyl 3,3-dimethylpent-4-enoate (0.18 g), toluene (0.13 g) and dibenzoyl peroxide (0.015 g) and the mixture heated at the reflux temperature (ca. 111° C.) for 2 hours. Determination of the resultant reaction mixture composition showed that the desired product had been produced to a yield of 82%, and that no sulphonylchloride remained.

CHEMICAL FORMULAE
(in description)

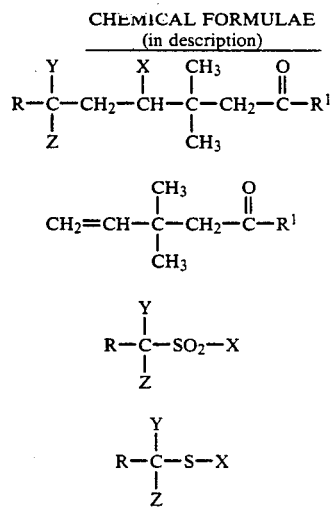

-continued
CHEMICAL FORMULAE
(in description)

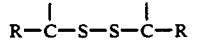

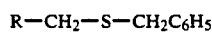

I claim:

1. A process for preparing a compound of formula:

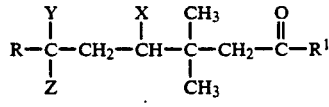

wherein X, Y and Z are each selected from halo, R is halo, alkyl, haloalkyl, or aryl which may optionally be substituted with halo, and $R^1$ is selected from hydroxy, halo, alkoxy, alkyl which may be substituted with halo, or $R^1$ represents a group $-OR^2$ derived from an alcohol $R^2OH$ esters of which with 3-(2,2-dichlorovinyl)-2,2-dimethylcyclopropane carboxylic acid are insecticidal, wherein a compound of formula:

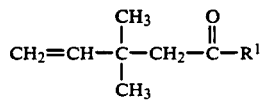

is reacted with a sulphonyl halide of formula:

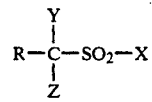

2. A process according to claim 1 wherein the compound of formula II is selected from methyl 3,3-dimethylpent-4-enoate, ethyl 3,3-dimethylpent-4-enoate and 2,6-dichlorobenzyl 3,3-dimethylpent-4-enoate.

3. A process according to claim 1 or claim 2 wherein the sulphonyl halide of formula III is selected from trichloromethane sulphonyl chloride and 1,1-dichloro-3,3,3-trifluoroethane sulphonyl chloride.

4. A process according to claim 1 conducted in the presence of an inert solvent.

5. A process according to claim 1 conducted in the presence of a free-radical catalyst.

6. A process according to claim 1 conducted at a temperature above the ambient temperature.

7. A process according to claim 1 where the sulphonyl halide of formula III is prepared by oxidation of the corresponding sulphenyl halide of formula:

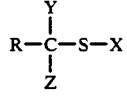

8. A process according to claim 7 wherein the sulphenyl halide is prepared by halogenolysis of either a disulphide of formula:

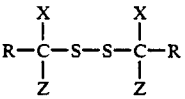

or a thioether of formula:

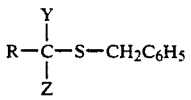

* * * * *